United States Patent
Garrone et al.

(10) Patent No.: US 11,752,147 B2
(45) Date of Patent: *Sep. 12, 2023

(54) PHARMACEUTICAL COMPOSITION FOR THE TREATMENT OF PAIN

(71) Applicant: AZIENDE CHIMICHE RIUNITE ANGELINI FRANCESCO A.C.R.A.F. S.p.A., Rome (IT)

(72) Inventors: Beatrice Garrone, Rome (IT); Lucia Durando, Rome (IT); Fabrizio Calisti, Rome (IT)

(73) Assignee: AZIENDE CHIMICHE RIUNITE ANGELINI FRANCESCO A.C.R.A.F. S.p.A, Rome (IT)

( * ) Notice: Subject to any disclaimer, the term of this patent is extended or adjusted under 35 U.S.C. 154(b) by 190 days.

This patent is subject to a terminal disclaimer.

(21) Appl. No.: 16/849,545

(22) Filed: Apr. 15, 2020

(65) Prior Publication Data

US 2020/0316060 A1 Oct. 8, 2020

Related U.S. Application Data

(62) Division of application No. 15/767,543, filed as application No. PCT/EP2016/074835 on Oct. 17, 2016, now Pat. No. 10,786,498.

(30) Foreign Application Priority Data

Oct. 22, 2015 (EP) .................................. 15191024

(51) Int. Cl.
| | | |
|---|---|---|
| A61K 31/496 | (2006.01) | |
| A61K 31/195 | (2006.01) | |
| A61K 45/06 | (2006.01) | |
| A61P 25/00 | (2006.01) | |

(52) U.S. Cl.
CPC .......... *A61K 31/496* (2013.01); *A61K 31/195* (2013.01); *A61K 45/06* (2013.01); *A61P 25/00* (2018.01)

(58) Field of Classification Search
CPC .................................................... A61K 31/496
See application file for complete search history.

(56) References Cited

U.S. PATENT DOCUMENTS

| | | |
|---|---|---|
| 2005/0059654 A1 | 3/2005 | Arneric et al. |
| 2008/0096872 A1 | 4/2008 | Friedman |
| 2010/0004485 A1 | 1/2010 | Cohen |
| 2011/0039875 A1 | 2/2011 | Singh |
| 2012/0083508 A1 | 4/2012 | Gil et al. |

FOREIGN PATENT DOCUMENTS

| | | |
|---|---|---|
| CN | 1878546 A | 12/2006 |
| EP | 1 663 398 B1 | 11/2009 |
| WO | WO 2009/021058 A2 | 2/2009 |
| WO | WO 2013/002584 A2 | 1/2013 |

OTHER PUBLICATIONS

International Search Report dated Dec. 12, 2016, in PCT/EP2016/074835 filed Oct. 17, 2016.
Wilson, R.C., "The Use of Low-Dose Trazodone in the Treatment of Painful Diabetic Neuropathy", Journal of the Americal Podiatric Medical Association, vol. 89, No. 9, (1999), pp. 468-471, XP009189323.
Okuda, K. et al., "Trazodone hydrochloride attenuates thermal hyperalgesia in a chronic constriction injury rat model", European Journal of Anaesthesiology, vol. 20, (2003), pp. 409-415, XP 009189324.
Ashburn, M.A. et al., "Management of chronic pain", The Lancet, vol. 353, (1999), pp. 1865-1869.
Woolf, C.J. et al., "Neuropathic pain: aetiology, symptoms, mechanisms, and management", The Lancet, vol. 353, (1999), pp. 1959-1964.
Kukkar, A. et al., "Implications and mechanism of action of gabapentin in neuropathic pain", Archives of Pharmacal Research, vol. 36, (2013), pp. 237-351.
Morillas-Arques, P. et al., "Trazodone for the treatment of fibromyalgia: an open-label, 12-week study", BMC Musculoskeletal Disorders, vol. 11, No. 204, (2010), 6 pages.
Calandre, E.P. et al., "Trazodone plus pregabalin combination in the treatment of fibromyalgia: a two-phase, 24-week, open-label uncontrolled study", BMC Musculoskeletal Disorders, vol. 12, No. 95, (2011), 9 pages.
Fernandez-Duenas, V. et al., "Fentanyl-trazodone-paracetamol triple drug combination: Multimodal analgesia in a mouse model of visceral pain", Pharmacology, Biochemistry and Behavior, vol. 98, (2011), pp. 331-336.
Scholz, J. et al., "Can we conquer pain?", Nature Neuroscience Supplement, vol. 5, (2002), pp. 1062-1067.
Stella, V.J. et al., "Prodrug strategies to overcome poor water solubility ☆", Sciencedirect, Advanced Drug Delivery Reviews, vol. 59, (2007), pp. 677-694.
Simplicio, A.L. et al., "Prodrugs for Amines", Molecules, vol. 13, ISSN 1420-3049, (2008), pp. 519-547.
Stock, J.L., "The prostaglandin E2 EP1 receptor mediates pain perception and regulates blood pressure", The Journal of Clinical Investigation, vol. 107, No. 3, (2001), pp. 325-331.
Seltzer, Z. et al., "A novel behavioral model of neuropathic pain disorders produced in rats by partial sciatic nerve injury", Pain, vol. 43, (1990), pp. 205-218.
Bennett, G.J. et al., "A peripheral mononeuropathy in rat that produces disorders of pain sensation like those seen in man", Pain, vol. 33, (1988), pp. 87-107.

*Primary Examiner* — Yong S. Chong

(74) *Attorney, Agent, or Firm* — Oblon, McClelland, Maier & Neustadt, L.L.P.

(57) ABSTRACT

The present invention relates to a pharmaceutical composition comprising a combination of trazodone or a salt thereof, and gabapentin or a salt or prodrug thereof, said combination having a synergistic effect in the treatment of pain.

8 Claims, 4 Drawing Sheets

(a)

(b)

(c)

(a)

trazodone:gabapentin ratio (b)

PHARMACEUTICAL COMPOSITION FOR THE TREATMENT OF PAIN

FIELD OF THE INVENTION

The present invention relates to a pharmaceutical composition comprising a combination of trazodone and gabapentin, said combination having a synergistic effect in the treatment of pain, in particular chronic pain.

BACKGROUND OF THE INVENTION

Physiological pain is an important protective mechanism designed to warn of danger from potentially injurious stimuli from the external environment.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered.

There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia).

Therefore pain can be divided into a number of different areas because of differing pathophysiology, these include nociceptive pain, inflammatory pain, chronic pain, neuropathic pain, and so on.

Nociceptive pain is induced by tissue injury or by intense stimuli with the potential to cause injury.

Neuropathic pain is defined as pain initiated or caused by a primary lesion or dysfunction in the nervous system.

The inflammatory process is a complex series of biochemical and cellular events activated in response to tissue injury or the presence of foreign substances, which result in swelling and pain. Arthritic pain makes up the majority of the inflammatory pain population. Rheumatoid disease is one of the commonest chronic inflammatory conditions in developed countries and rheumatoid arthritis is a common cause of disability. Other types of inflammatory pain include but are not limited to inflammatory bowel diseases (IBD).

Chronic pain represents a series of pathologies from which, on average, about 10-20% of the adult population suffers. Chronic pain is generally associated with clinical conditions characterized by chronic and/or degenerative lesions.

Chronic pain differs from acute pain mainly by the duration. Acute pain has a duration of a few days or weeks, correlated with recovery from the event that caused the pain (trauma, burns, intense efforts, surgical or dental interventions, and the like). On the other hand, chronic pain persists for months and even years, causing muscular tension, limited mobility, fatigue, loss of appetite and apathy.

Typical examples of pathologies characterized by chronic pain are rheumatoid arthritis, osteoarthritis, fibromyalgia, neuropathies, etc. [Ashbum Mass., Staats PS. Management of chronic pain. Lancet 1999; 353: 1865-69].

Chronic pain, and in particular neuropathic pain, is often debilitating and is a cause of loss of working capacity and of poor quality of life. Economic and social damage thus also follow.

The analgesic drugs currently used in the treatment of neuropathic pain include non-steroidal anti-inflammatory drugs (NSAID), anti-depressants, opioid analgesics, and anticonvulsants [Woolf C J, Mannion R J, Neuropathic pain: aetiology, symptoms, mechanism, and management. Lancet 1999; 353: 1959-1964].

However, chronic pain, and in particular neuropathic pain, is notoriously difficult to treat with the drugs currently available. Consequently, the development of novel drugs has always been one of the main objectives of the pharmaceutical industry.

EP1663398B1 discloses a combination of an alpha-2-delta ligand such as gabapentin and pregabalin with a selective noradrenaline re-uptake inhibitor such as (S,S)-reboxetine for the treatment of neuropathic pain.

WO 2013/002584 discloses a pain suppressive composition comprising two or more components selected from (a) 5-HT2 receptor antagonist, (b) a P2X receptor antagonist, and (c) any one of glycine receptor agonist, a glycine transporter antagonist, a gamma-aminobutyric acid (GABA) receptor agonist, and a GABA transporter 1 (GABA1) antagonist.

A review of the use of gabapentin in the treatment of neuropathic pain has been published by Kukkar A. et al, "Implications and mechanism of action of gabapentin in neuropathic pain", Arch. Pharm. Res. (2013) 36:237-251. A superior effect was observed by the combination of gabapentin and venlafaxine in the rat spared nerve injury (SNI) model of neuropathic pain and by co-administration of gabapentin with donepezil and/or duloxetine against spinal nerve ligation-induced neuropathic pain and in spared nerve injury model.

Trazodone and a combination of trazodone and pregabalin have been studied in a 12- and 24-week treatment of fibromyalgia as disclosed in Morillas-Arques et al., "Trazodone for the treatment of fibromyalgia: an open-label, 12-week study", BMC Musculoskeletal Disorders 2010, 11:204 and Calandre et al., "Trazodone plus pregabalin combination in the treatment of fibromyalgia: a two-phase, 24-week, open-label uncontrolled study", BMC Musculoskeletal Disorders 2011, 12:95.

A combination of trazodone with fentanyl and paracetamol has been studied in a mouse model of visceral pain, showing a potent synergistic antinociceptive effect, as disclosed in Fernández-Dueñas et al., "Fentanyl-trazodone-paracetamol triple drug combination: Multimodal analgesia in a mouse model of visceral pain", Pharmacology, Biochemistry and Behavior 98 (2011) 331-336.

Despite the numerous research efforts directed towards identifying a suitable analgesic compound, there is a significant number of patients whose pain condition still lacks a suitable treatment [Scholz J, Woolf C J. Can we conquer pain? Nat Neusci. 2002; 5: 1062-76] and there is a continuous need to find novel treatments able to improve the patient conditions.

SUMMARY OF THE INVENTION

The Applicant faced the problem to provide a pharmaceutical composition for the treatment of pain, in particular chronic pain, having an improved activity when compared to the compositions known in the art.

The Applicant has found that trazodone can be used in association with gabapentin.

In particular, the Applicant has now surprisingly found that the combination of trazodone with gabapentin has a synergistic effect in reducing pain in two experimental models in rats represented by (i) the inflammatory pain induced by injection of acetic acid, and (ii) the chronic pain induced by ligature of the sciatic nerve.

As is known to those skilled in the art, the abovementioned experimental models may be considered as predictive of activity in man.

The experimental model of injection of acetic acid in rats represents an evaluation of the antinociceptive activity of the combination of the invention in a model of inflammatory pain.

Typical examples of human pathologies characterized by the dysfunctions described in the abovementioned experimental model and characterized by the presence of inflammatory pain are oedema, erythema, articular inflammation, osteoarthritis, rheumatoid arthritis and arthrosis.

The experimental model of ligature of the sciatic nerve in rats represents a neuropathy that reproduces a series of responses similar to those observed in man in numerous traumatic and pathological conditions associated with neuropathic pain. The reason for this is that ligature of the sciatic nerve is capable of inducing a syndrome associated with the activation of specific circuits dedicated to controlling the perception of pain and characterized by the appearance of allodynia, hyperalgesia and spontaneous pain. This model is well known to constitute a valid instrument for studying drugs to be used in the treatment of neuropathic pain in man, and in particular in controlling conditions such as allodynia and hyperalgesia.

Typical examples of human pathologies characterized by the dysfunctions described in the abovementioned experimental model and characterized by the presence of neuropathic pain are diabetes, cancer, immunodeficiency, trauma, ischemia, multiple sclerosis, sciatica, trigeminal neuralgia, fibromyalgia and post-herpetic syndrome.

Thus, in a first aspect, the present invention relates to a pharmaceutical composition comprising a synergistic combination of trazodone or a salt thereof, and gabapentin or a salt or prodrug thereof, and at least one pharmaceutically acceptable excipient, for use in the treatment of pain.

A second aspect of the present invention relates to a method for the treatment of pain, comprising administering to a subject in need thereof a synergistically effective amount of trazodone or a salt thereof and gabapentin or a salt or prodrug thereof.

BRIEF DESCRIPTION OF THE DRAWINGS

In FIG. 3a, the inhibition percentage, expressed with reference to the result obtained with the vehicle, is reported on the Y axis for each group of mice administered with trazodone and gabapentin alone or in combination with a weight ratio as reported on the X axis. FIG. 3b only reported on the Y axis the inhibition percentage of the trazodone/gabapentin combination with a weight ratio as reported on the X axis.

DETAILED DESCRIPTION OF THE INVENTION

Figure 1:
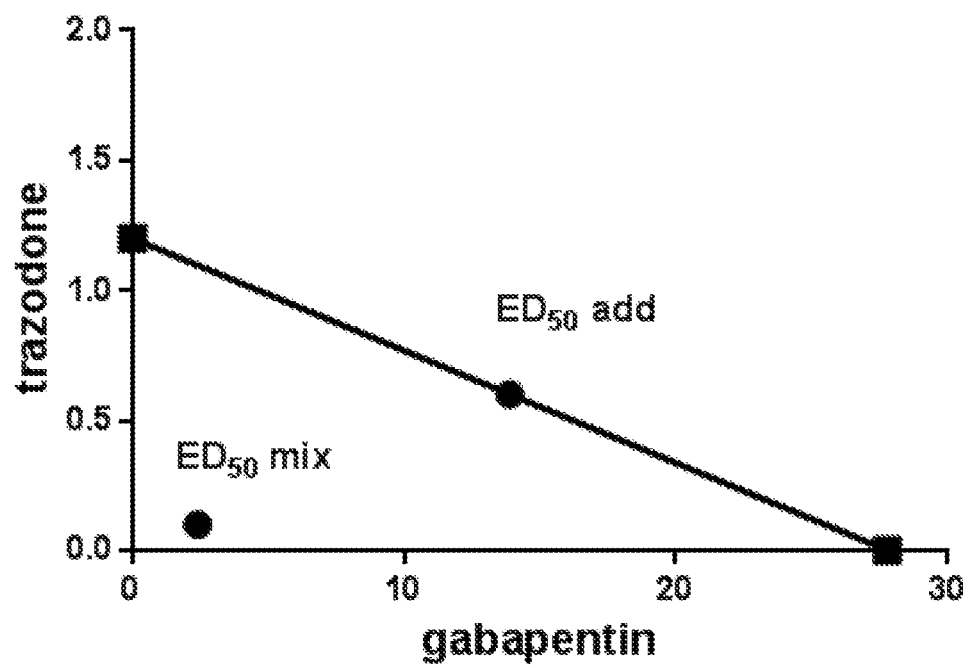
FIG. 1 visually shows the results of example 1. The $ED_{50}$ values of each drug (trazodone and gabapentin) are plotted on the X and Y axis. The line connecting both points is the theoretical line of additivity. The experimental $ED_{50}$ value of the trazodone and gabapentin combination ($ED_{50}$mix) is found significantly below the theoretical additive $ED_{50}$ value ($ED_{50}$add).

In the present description, the expression "synergistic effect" means that the combination of trazodone with gabapentin inhibits the pain response in mice or rats at a concentration lower than the sum of the concentrations of trazodone and of gabapentin used alone for the same pain test to obtain the same inhibition. In other words, a synergistic effect means that the combination of trazodone with gabapentin is effective in producing more than the additive effect of each component in the same pain test.

The pharmaceutical composition according to the present invention comprises trazodone or a salt thereof in an amount to provide an ineffective dosage if taken alone.

Preferably, the pharmaceutical composition according to the present invention contains trazodone or a salt thereof in an amount to provide a dosage equal to or lower than 1 mg/kg, more preferably equal to or lower than 0.5 mg/kg, and even more preferably equal to or lower than 0.2 mg/kg.

Preferably, the pharmaceutical composition according to the present invention contains trazodone or a salt thereof in an amount to provide a dosage equal to or higher than 0.01 mg/kg, more preferably equal to or higher than 0.05 mg/kg, and even more preferably equal to or higher than 0.1 mg/kg.

Accordingly, the pharmaceutical composition according to the present invention may contain trazodone or a salt thereof in any amount able to provide a dosage ranging from 0.01 mg/kg to 1 mg/kg, preferably ranging from 0.05 mg/kg to 0.5 mg/kg, more preferably from 0.1 mg/kg to 0.2 mg/kg, such as, for example, 0.02, 0.04, 0.07, 0.11, 0.12, 0.13, 0.14, 0.15, 0.16, 0.17, 0.18, 0.19, 0.2, 0.25, 0.3, 0.4, 0.6, 0.7, 0.8, and 0.9 mg/kg, and the like.

Advantageously, the pharmaceutical composition according to the present invention contains trazodone or a salt thereof in an amount to provide a dosage equal to about 0.15 mg/kg.

Accordingly, the pharmaceutical composition according to the present invention may contain trazodone or a salt thereof in an amount equal to or lower than 70 mg, more preferably equal to or lower than 35 mg, and even more preferably equal to or lower than 15 mg.

The pharmaceutical composition according to the present invention comprises gabapentin or a salt or prodrug thereof in an amount to provide an ineffective dosage if taken alone.

Preferably, the pharmaceutical composition according to the present invention contains gabapentin or a salt or prodrug thereof in an amount to provide a dosage equal to or lower than 15 mg/kg, more preferably equal to or lower than 5 mg/kg, and even more preferably equal to or lower than 2 mg/kg.

Preferably, the pharmaceutical composition according to the present invention contains gabapentin or a salt or prodrug thereof in an amount to provide a dosage equal to or higher than 0.1 mg/kg, more preferably equal to or higher than 0.5 mg/kg, and even more preferably equal to or higher than 1 mg/kg.

Accordingly, the pharmaceutical composition according to the present invention may contain gabapentin or a salt or prodrug thereof in any amount able to provide a dosage ranging from 0.1 mg/kg to 15 mg/kg, preferably ranging from 0.5 mg/kg to 5 mg/kg, more preferably from 1 mg/kg to 2 mg/kg, such as, for example, 0.2, 0.4, 0.7, 1.1, 1.2, 1.3, 1.4, 1.5, 1.6, 1.7, 1.8, 1.9, 2.0, 2.5, 3.0, 4.0, 6.0, 7.0, 8.0, and 9.0 mg/kg, and the like.

Advantageously, the pharmaceutical composition according to the present invention contains gabapentin or a salt or prodrug thereof in an amount to provide a dosage equal to about 1.5 mg/kg.

Accordingly, the pharmaceutical composition according to the present invention may contain gabapentin or a salt or prodrug thereof in an amount equal to or lower than 1000 mg, more preferably equal to or lower than 350 mg, and even more preferably equal to or lower than 150 mg.

Advantageously, the pharmaceutical composition according to the present invention contains an amount of trazodone or a salt thereof and an amount of gabapentin or a salt or prodrug thereof such as to provide a trazodone to gabapentin weight ratio ranging from 1:40 to 10:1, preferably from 1:20 to 1:1, and more preferably from 1:15 to 1:5.

Any value within the above mentioned trazodone to gabapentin weight ratio can be used, such as, for example, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, and 9:1.

Advantageously, the pharmaceutical composition according to the present invention contains an amount of trazodone or a salt thereof and an amount of gabapentin or a salt or prodrug thereof such as to provide a trazodone to gabapentin weight ratio of about 1:10.

Prodrugs of gabapentin are included in the scope of the instant invention. The chemically modified drug, or prodrug, should have a different pharmacokinetic profile to the parent, enabling easier absorption across the mucosal epithelium, better salt formulation and/or solubility, improved systemic stability (for an increase in plasma half-life, for example).

These chemical modifications may be (i) ester derivatives (ii) amide derivatives, (iii) carbamate derivatives, (iv) N-acyloxyalkyl derivatives, (v) N-acyloxyalkoxycarbonyl derivatives, (vi) peptides, and (vii) any combination thereof.

The ester can be derived from the carboxylic acid moiety of the drug molecule by known means. The amide may be derived from the carboxylic acid moiety or the amine moiety of the drug molecule by known means. Ester or amide derivatives may be cleaved by, for example, esterases or lipases.

The peptide may be coupled to the drug molecule via amide bond formation with the amine or carboxylic acid moiety of the drug molecule by known means. Peptides may be recognized by specific or nonspecific proteinases.

The carbamate, N-acyloxyalkyl and N-acyloxyalkoxycarbonyl can be derived from the amine moiety of the drug molecule by known means. Such derivatives can be cleaved by esterases and/or decomposes spontaneously.

Useful examples of suitable prodrugs are described, for example, in Stella V. J. et al, "Prodrug strategies to overcome poor water solubility", Advance Drug Delivery Reviews 59 (2007) 677-694, and in Simplicio A. L. et al., "Prodrugs for Amines", Molecules 2008, 13, 519-547.

An advantageously useful example of gabapentin prodrug is the compound (1-{[({(1RS)-1-[isobutyryloxy]ethoxy}carbonyl)amino] methyl} cyclohexyl) acetic acid, commonly known as gabapentin enacarbil.

Salts of trazodone and gabapentin are included in the scope of the instant invention. The salt can be formed with physiologically acceptable organic and inorganic compounds having an acid or a basic function.

Typical examples of suitable physiologically acceptable inorganic acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, paratoluenesulfonic acid, benzenesulfonic acid, succinic acid, tannic acid and tartaric acid.

Typical examples of suitable physiologically acceptable inorganic bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylam inoethanol, 2-dimethylaminoethanol, etha-nolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

Preferably, the pharmaceutical composition according to the present invention is for systemic use.

More preferably the pharmaceutical composition according to the present invention is formulated for oral or parenteral administration.

Preferably, the pharmaceutical composition according to the present invention is prepared in suitable dosage forms.

Examples of suitable dosage forms are tablets, capsules, coated tablets, granules, and solutions and syrups for oral administration; creams, ointments transdermal patch and antiseptic plasters for topical administration; suppositories for rectal administration and sterile solutions for administration by injection, or aerosol or ophthalmic administration.

The dosage forms of the pharmaceutical composition of the present invention may be prepared according to techniques that are well known to pharmaceutical chemists, including mixing, granulation, tableting, dissolution, sterilization and the like.

Advantageously, these dosage forms are formulated so as to ensure a controlled release over time of a compound of the abovementioned general formula (I) or of a pharmaceutically acceptable salt thereof. Specifically, depending on the type of therapy, the required release time may be very short, normal or long.

The pharmaceutically acceptable excipient can be selected from the group comprising thickeners, glidants, binders, disintegrants, fillers, diluents, preservative, stabilizers, surfactants, buffers, fluidizers, lubricants, humectants, absorbents, salts for regulating osmotic pressure, emulsifiers, flavorings, colorants, sweeteners, and the like.

The pharmaceutical composition according to the present invention is effective for the treatment of pain.

The Applicant has found that the combination of trazodone with gabapentin has a synergistic effect in reducing pain in two experimental models in animals represented by (i) the inflammatory pain induced in mice by injection of acetic acid, and (ii) the chronic pain induced in rats by ligature of the sciatic nerve.

Accordingly, the pharmaceutical composition according to the present invention can be used to treat effectively and with high safety all kinds of chronic pain, either inflammatory or neuropathic in origin.

Preferred examples of chronic pain treated according to the present invention are the following:

inflammatory pain induced by oedema, erythema, articular inflammation, osteoarthritis, rheumatoid arthritis and arthrosis; and neuropathic pain induced by diabetes, cancer, immunodeficiency, trauma, ischemic, multiple sclerosis, sciatica, trigeminal neuralgia, fibromyalgia and post-herpetic syndrome.

The examples that follow are intended for further illustration of the present invention, though without limiting it.

EXAMPLES

Description of the Test Methods

Writhing Test in Mice

The test compounds were evaluated in the model of acetic acid-induced writhing in mice (Stock J. L. et al., J. Clin. Inv. 2001, 107: 325 331).

Writhing test is a chemical method used to induce pain of peripheral origin by injection of acetic acid in mice. Analgesic activity is inferred from decrease in the frequency of writhing.

This test allowed evaluation of the antinociceptive activity of the compounds of the invention in a model of inflammatory pain.

Writhing is defined as a stretch, tension to one side, extension of hind legs, contraction of the abdomen so that the abdomen of mice touches the floor, turning the trunk (twist).

Male CD-1 mice weighing 20-25 g were used for the test.

The mice were orally treated with trazodone and gabapentin alone and in combination, or vehicle such as distilled water.

One hour after the treatment, an intraperitoneal injection of acetic acid (0.7% v/v in physiological saline, 16 µl/g of body weight) was given to the mice to induce inflammatory pain and to check the effects of the test compound on the nociceptive response.

Five minutes after the administration of acetic acid and for the following 10 minutes the number of writhes was measured, which represents the parameter for evaluation of the nociceptive response. The analgesic activity is evaluated as % inhibition.

Ligature of the Sciatic Nerve in Rats

Male CD rats weighing 200-250 g on arrival were used.

The allodynia was induced by ligature under anaesthesia of the sciatic nerve of the left hind leg [Seltzer Z, Dubner R, Shir Y. A novel behavioural model of neuropathic pain disorders produced in rats by partial sciatic nerve injury. Pain 1990; 43: 205-218; Bennet G J, Xie Y K. A peripheral mononeuropathy in rat that produces disorders of pain sensation like those seen in man. Pain 1988; 33: 87-107].

Two weeks after ligature of the sciatic nerve, rats who showed a reduction of at least 50% in the response threshold recorded before the intervention were selected. The pain threshold was measured with a von Frey machine, which makes it possible, by applying a gradual increase in pressure to the paw of the left hind leg of the rat, to record the nociceptive response, expressed in grams, corresponding to the moment at which the animal withdraws the leg.

Immediately after a pre-treatment measurement, the rats were treated with trazodone and gabapentin alone and in combination, or vehicle such as distilled water. After-treatment measurement was made at one hour following administration. The analgesic activity is evaluated as % reversal.

Results

Example 1

The ED50 values of trazodone, gabapentin and trazodone/gabapentin combination with a trazodone/gabapentin weight ratio equal to 1/10 has been determined using the writhing test in mice.

The results are summarized in the following Table 1.

TABLE 1

| Drug(s) | ED50 (mg/kg) |
| --- | --- |
| Trazodone | 1.2 |
| Gabapentin | 27.8 |
| Trazodone/Gabapentin | 2.5 |

As illustrated in the FIG. 1, the theoretical additive ED50 of the trazodone/gabapentin combination should have been 14.5 mg/kg, so resulting in an interaction index of about 0.17, providing a strong indication of synergistic interaction.

Example 2

The writhing test in mice was repeated by administering to four groups of mice ineffective increasing amounts of trazodone and gabapentin alone, or in combination with a trazodone/gabapentin weight ratio equal to 1/10, according to the following Table 2, and vehicle alone.

Figure 2:
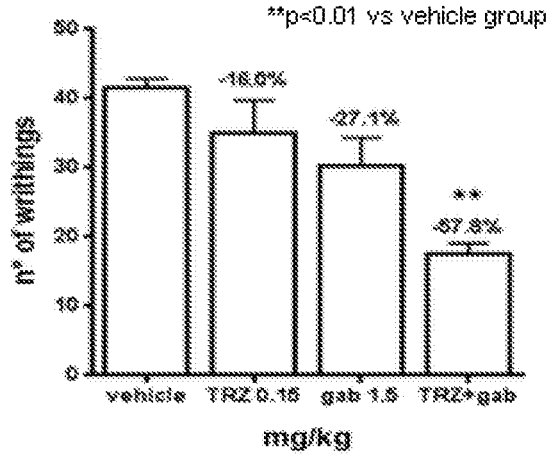
FIG. 2 visually shows the results of example 2. The number of writhing counted within the 10 minutes after the administration of acetic acid are reported on the Y axis for each group of mice administered with the vehicle or ineffective amounts of trazodone and gabapentin alone or in combination as reported on the X axis.
Figure 2:
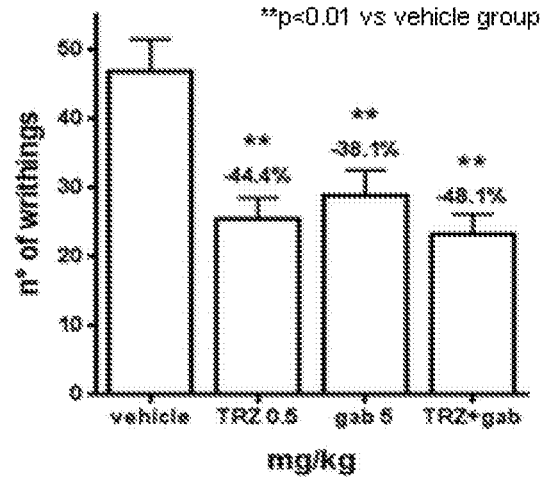
Figure 2:
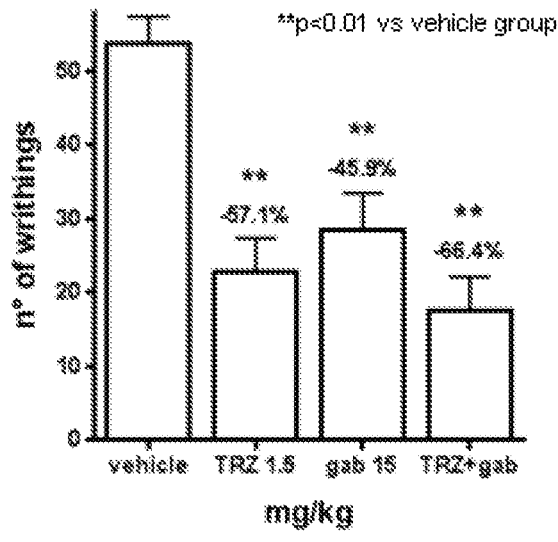

The results of each test, expressed as reduction percentage of writhing number compared with the vehicle, are summarized in Table 2 and illustrated in FIGS. 2a, 2b and 2c.

TABLE 2

| Drug(s) | Amount (mg/kg) | Writhing number reduction % |
| --- | --- | --- |
| TEST 1 - FIG. 2a | | |
| Trazodone | 0.15 | 16.0 |
| Gabapentin | 1.5 | 27.1 |
| Trazodone/Gabapentin | 0.15/1.5 | 57.8 |
| TEST 2 - FIG. 2b | | |
| Trazodone | 0.5 | 44.4 |
| Gabapentin | 5 | 38.1 |
| Trazodone/Gabapentin | 0.5/5 | 48.1 |
| TEST 3 - FIG. 2c | | |
| Trazodone | 1.5 | 57.1 |
| Gabapentin | 15 | 45.9 |
| Trazodone/Gabapentin | 1.5/1.5 | 66.4 |

The results surprisingly demonstrated that the synergistic effect of the combination of trazodone gabapentin were evident only at the lowest dosage of trazodone and gabapentin employed in test 1.

Example 3

The writhing test in mice was repeated by administering to four groups of mice different ineffective amounts of trazodone and gabapentin alone, or in combination with different trazodone/gabapentin weight ratio, according to the following Table 3, and vehicle alone.

Figure 3:
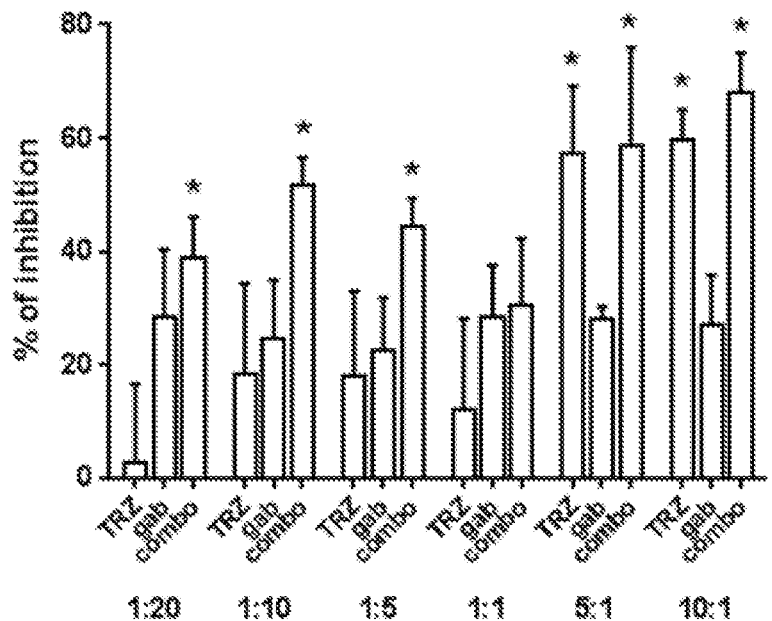
FIG. 3 visually shows the results of example 3.
Figure 3:
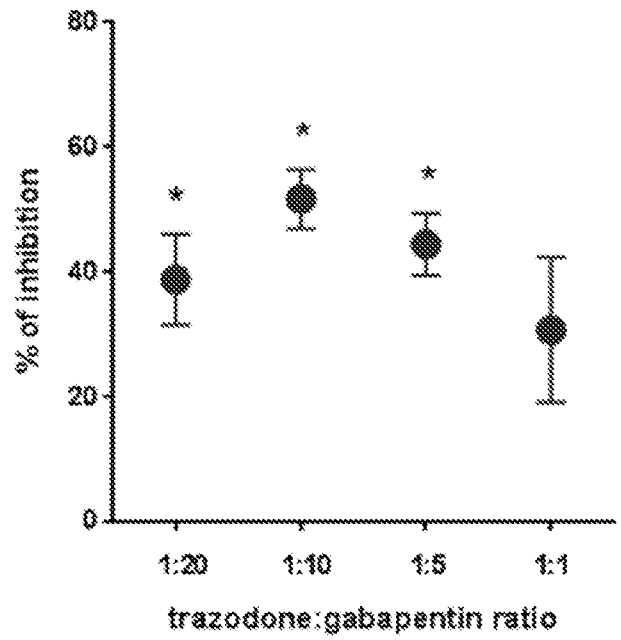

The results of each test, expressed as reduction percentage of writhing number compared with the vehicle, are summarized in Table 3 and illustrated in FIGS. 3a and 3b.

TABLE 3

| Drug(s) | Amount (mg/kg) | Writhing number reduction % |
|---|---|---|
| TEST 1 - RATIO 1:20 | | |
| Trazodone | 0.075 | 2.1 |
| Gabapentin | 1.5 | 29.2 |
| Trazodone/Gabapentin | 0.075/1.5 | 47.6 |
| TEST 2 - RATIO 1:10 | | |
| Trazodone | 0.15 | 16.0 |
| Gabapentin | 1.5 | 27.1 |
| Trazodone/Gabapentin | 0.15/1.5 | 57.8 |
| TEST 3 - RATIO 1:5 | | |
| Trazodone | 0.15 | 16.3 |
| Gabapentin | 0.75 | 22.4 |
| Trazodone/Gabapentin | 0.15/0.75 | 44.4 |
| TEST 4 - RATIO 1:1 | | |
| Trazodone | 0.15 | 12.2 |
| Gabapentin | 0.15 | 28.3 |
| Trazodone/Gabapentin | 0.15/0.15 | 30.7 |
| TEST 5 - RATIO 5:1 | | |
| Trazodone | 0.75 | 57.4 |
| Gabapentin | 0.15 | 30.2 |
| Trazodone/Gabapentin | 0.75/0.15 | 58.5 |
| TEST 6 - RATIO 10:1 | | |
| Trazodone | 1.5 | 59.7 |
| Gabapentin | 0.15 | 27.2 |
| Trazodone/Gabapentin | 1.5/0.15 | 67.9 |

The results surprisingly demonstrated that the combination of trazodone and gabapentin having a trazodone/gabapentin weight ratio equal to 1:10 showed the most enhanced synergistic analgesic activity.

Example 4

The test of ligature of the sciatic nerve in rats was employed to confirm the synergic effect of the combination of trazodone and gabapentin in the treatment of chronic neuropathic pain.

The test was done by administering to five groups of rats ineffective amounts of trazodone and gabapentin alone, or in combination with a trazodone/gabapentin weight ratio equal to 1:10, and an effective amount of gabapentin according to the following Table 4 and vehicle alone.

Figure 4:
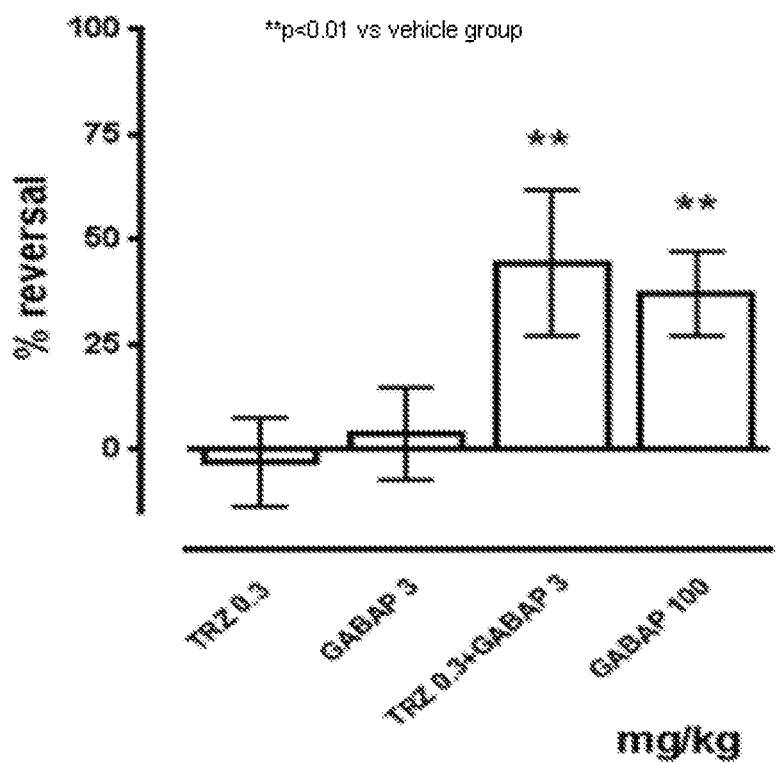
FIG. 4 visually shows the results of example 4. The reversal percentage, expressed with reference to the result obtained with the vehicle, is reported on the Y axis for each group of rats administered with trazodone and gabapentin alone or in combination as reported on the X axis.

The results of the test, expressed as reversal percentage compared with the vehicle, are summarized in Table 4 and illustrated in FIG. 4.

TABLE 4

| Drug(s) | Amount (mg/kg) | Reversal % |
|---|---|---|
| Trazodone | 0.3 | 3.1 |
| Gabapentin | 3.0 | 3.7 |
| Trazodone/Gabapentin | 0.3/3.0 | 44.3 |
| Gabapentin | 100 | 37.0 |

The results confirmed the synergic effect of the combination of trazodone and gabapentin in the treatment of chronic neuropathic pain, which resulted in an activity even higher than the activity obtained with a conventional effective dose of gabapentin alone.

The invention claimed is:

1. A method of treating pain, comprising administering to a subject in need thereof trazodone or a salt thereof and gabapentin or a salt or prodrug thereof as the only active agents in a combined effective synergistic amount, wherein said pain is selected from the group consisting of chronic pain, inflammatory pain, and neuropathic pain, wherein said trazodone or a salt thereof is administered in an amount equal to or lower than 0.2 mg/kg and said gabapentin or a salt or prodrug thereof is administered in an amount equal to or lower than 2 mg/kg, and wherein the trazodone or salt thereof and gabapentin or a salt or prodrug thereof weight ratio is from 1:15 to 1:5.

2. The method according to claim 1, wherein said pain is chronic pain.

3. The method according to claim 1, wherein said pain is inflammatory pain induced by oedema, erythema, articular inflammation, osteoarthritis, rheumatoid arthritis, or arthrosis.

4. The method according to claim 1, wherein said pain is neuropathic pain.

5. The method according to claim 1, wherein said pain is neuropathic pain induced by diabetes, cancer, immunodeficiency, trauma, ischemia, multiple sclerosis, sciatica, trigeminal neuralgia, fibromyalgia, or post-herpetic syndrome.

6. The method according to claim 1, wherein said pain is neuropathic pain induced by diabetes.

7. The method according to claim 1, which comprises administering trazodone or a salt thereof in an amount equal to about 0.15 mg/kg and gabapentin or a salt or prodrug thereof in an amount equal to about 1.5 mg/kg.

8. The method according to claim 1, which comprises administering trazodone or a salt thereof and gabapentin or a salt or prodrug thereof in a trazodone to gabapentin weight ratio of about 1:10.

* * * * *